United States Patent [19]

Hildon et al.

[11] 4,177,196

[45] * Dec. 4, 1979

[54] EPOXIDATION

[75] Inventors: Anthony M. Hildon, Tattenhall; Peter F. Greenhalgh, Widnes, both of England

[73] Assignee: Interox Chemicals Limited, London, England

[*] Notice: The portion of the term of this patent subsequent to Jan. 31, 1995, has been disclaimed.

[21] Appl. No.: 806,944

[22] Filed: Jun. 15, 1977

Related U.S. Application Data

[63] Continuation-in-part of Ser. No. 649,747, Jan. 16, 1976, Pat. No. 4,071,541.

[51] Int. Cl.$^2$ .................. C07D 301/14; C07C 179/10; C07C 179/12
[52] U.S. Cl. ............................ 260/348.25; 260/502 R
[58] Field of Search ........................ 260/348.25, 502 R

[56] References Cited

U.S. PATENT DOCUMENTS 3,799,949  3/1974  Keller ............................ 260/348.5 L

FOREIGN PATENT DOCUMENTS 1048569  1/1959  Fed. Rep. of Germany.
2141156  3/1973  Fed. Rep. of Germany.
2262970  7/1974  Fed. Rep. of Germany.
1188791  4/1970  United Kingdom.

*Primary Examiner*—Norma S. Milestone
*Attorney, Agent, or Firm*—Larson, Taylor and Hinds

[57] ABSTRACT

The invention provides a continuous process for the production of a peracid in a chlorinated hydrocarbon solvent comprising the steps of: (a) providing an aqueous phase comprising sulphuric acid, hydrogen peroxide and water; (b) providing an organic phase comprising a chlorinated hydrocarbon solvent and carboxylic acid selected from the group consisting of acetic acid and propionic acid; and (c) contacting said aqueous and organic phases countercurrently to produce an aqueous solution comprising sulphuric acid and water and an organic product solution comprising chlorinated hydrocarbon solvent and a peracid corresponding to said carboxylic acid. Desirably the process includes the added step of: (d) utilizing at least a portion of said aqueous solution to provide at least a portion of the aqueous phase of step (a).

8 Claims, 2 Drawing Figures

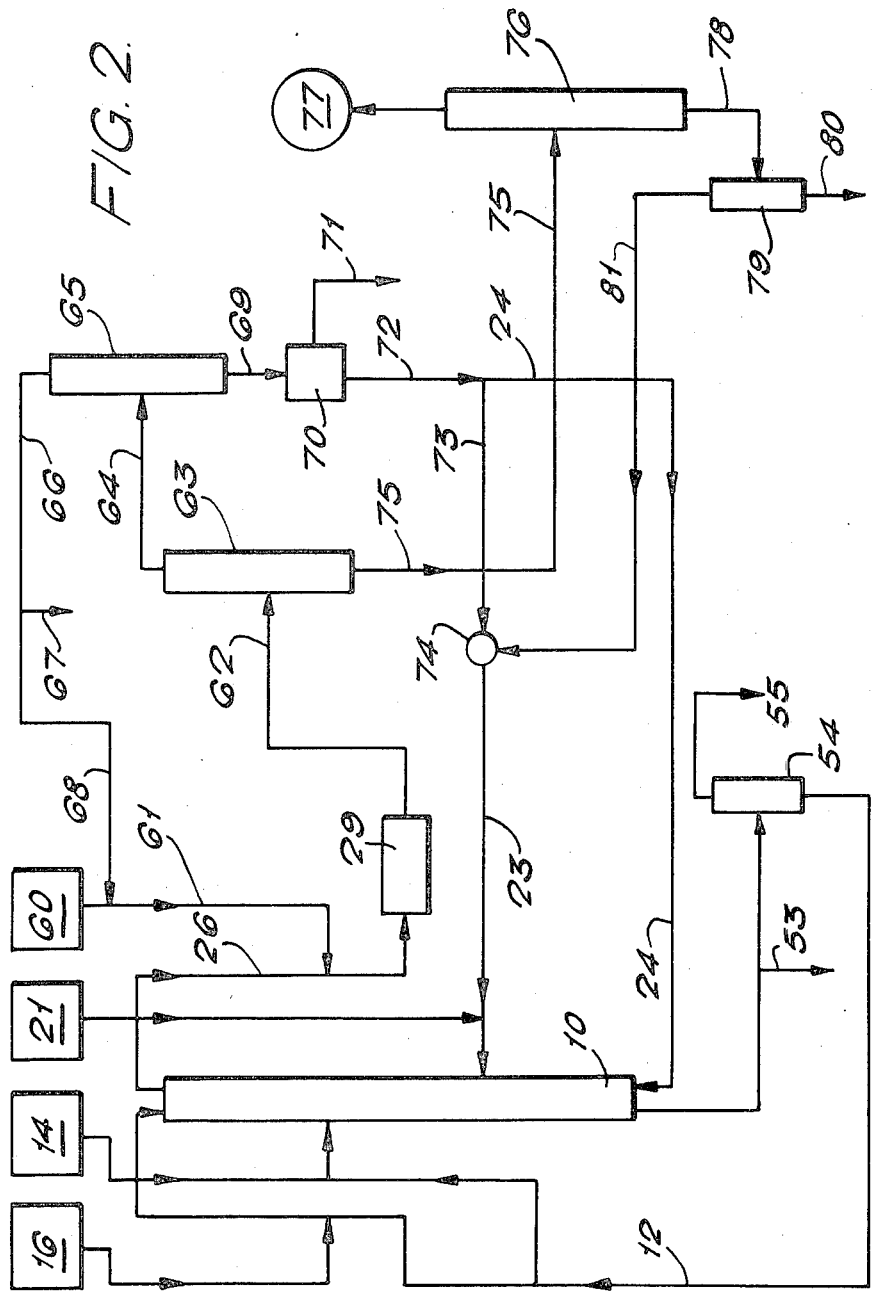

EPOXIDATION

This application is a continuation-in-part of co-pending application Ser. No. 649,747, filed Jan. 16, 1976, now U.S. Pat. No. 4,071,541 issued Jan. 31, 1978.

The present invention relates to the epoxidation of alkenes and more specifically lower alkenes.

The term "alkene" is used herein to mean the mono-unsaturated compounds and to include substituted compounds where the substitution will not prevent epoxidation.

In one aspect, the invention relates to a process for the production of a peracid (otherwise known as a "peroxycarboxylic acid") in a chlorinated hydrocarbon solvent. In another aspect, the invention relates to use of the peracid in the epoxidation reaction. The product of the epoxidation reaction is called an "oxirane" or "epoxide".

Although the present invention can be applied to ethylene, the lowest alkene, it is not thought that the reaction would be economically attractive at the present time as compared with the direct oxidation of ethylene. It would appear that the invention is likely to prove most advantageous when applied to propylene and chlor- or hydroxyl- substituted propylene. Propylene is otherwise known as propene; the chloro-substituted compound is allyl chloride or 3-chloro-propene and the hydroxyl-substituted compound is allyl alcohol or 2-propen-1-ol. Throughout this specification the term "propene" will be used to include these substituted compounds and the terms "propylene", "allyl chloride" and "allyl alcohol" will refer to the specific compounds. It will be apparent that the corresponding oxiranes are epoxypropane, propylene oxide, epichlorhydrin and glycidol.

The invention also appears to be economically attractive when applied to butene. The term "butene" is intended to include both straight and branched chain isomers and internal and external olefins together with their substituted compounds.

The invention can also be applied to the various pentenes and to higher alkenes.

Various prior art suggestions, dating back to 1909, relate to the general reaction between olefins and peracids and it has hitherto been preferred to use either peracetic or performic acid. D. Swern in Chem. Rev. 1945 p 1-68 comments that it is necessary to employ peracetic acid in an inert solvent in order to obtain good yields of oxirane compounds. He believed this to be a serious drawback to the general applicability of peracetic acid for epoxidation and stated, correctly, that the preparation of peracetic acid free from acetic acid is normally very difficult.

Dealing more specifically with the production of propylene oxide, it has been suggested in U.K. Pat. No. 900836 that peracetic acid can be used in solution in acetic acid, optionally in admixture with acetone or methylal. However the same patentees in U.S. Pat. No. 3,341,556 suggest that the amount of acetic acid should be strictly controlled and that the acetone or some other solvent is necessary.

Having studied this prior art, we have come to the conclusion that it is preferable to use peracetic or perpropionic acid as these show marked advantages over perbutyric or performic acid, the latter being suggested in U.K. Pat. No. 1188791. The use of anhydrous perpropionic acid in the production of chloroepoxides is disclosed in U.K. Pat. No. 784620.

U.K Pat. No. 1188791 also deals with the production of performic acid using an inert solvent, but it has not been suggested that a similar process can be applied to the production of perpropionic acid.

According to the present invention there is provided a process for epoxidation of an alkene by reaction with a peracid, characterised by supplying an aqueous phase comprising sulphuric acid, hydrogen peroxide and water and an organic phase comprising acetic acid or propionic acid in a chlorinated hydrocarbon solvent to a liquid-liquid extraction device in such manner that these two phases pass in countercurrent through the extraction device; withdrawing from such extraction device an organic solution of peracid and carboxylic acid in the chlorinated hydrocarbon; passing said organic solution and the alkene cocurrently to a reactor; withdrawing from the reactor a product mixture and effecting fractional distillation thereof; withdrawing from such fractional distillation a product phase comprising the oxirane and a recycle phase comprising carboxylic acid in the chlorinated hydrocarbon, and passing such recycle phase from the distillation to the extraction device to form the organic phase therein.

It must be emphasised that the importance of this process resides in the integration of the preparation of the oxirane by epoxidation of the alkene by the peracid with the production of the peracid from a carboxylic acid and hydrogen peroxide.

In another aspect there is provided, according to the present invention, a continuous process for the production of a peracid in a chlorinated hydrocarbon solvent comprising the steps of: (a) providing an aqueous phase comprising sulphuric acid, hydrogen peroxide and water; (b) providing an organic phase comprising a chlorinated hydrocarbon solvent and carboxylic acid selected from the group consisting of acetic acid and propionic acid; and (c) contacting said aqueous and organic phases countercurrently to produce an aqueous solution comprising sulphuric acid and water and an organic product solution comprising chlorinated hydrocarbon solvent and a peracid corresponding to said carboxylic acid. Desirably, the process includes the added step of utilizing at least a portion of said aqueous solution to provide at least a portion of the aqueous phase of step (a).

Although the broad term "chlorinated hydrocarbon" is used herein, it should be understood that there are many practical constraints on the solvent which can be used. Thus the solvent must be non-reactive to all the other components of the system and must be readily separable from the product and recoverable from the various waste stream. We prefer to use propylene dichloride (otherwise called 1,2-dichloropropane) but it is also possible to use dichloromethane, trichloromethane, tetrachloromethane, chloroethane, 1,1-dichloroethane, 1,2-dichloroethane, 1,1,1-trichloroethane, 1,1,2-trichloroethane, 1,1,1,2-tetrachloroethane, 1,1,2,2-tetrachloroethane, 1-chloropropane, 2-chloropropane, 1,1-dichloropropane, 1,3-dichloropropane, 2,2-dichloropropane, 1,1,1-trichloropropane, 1,1,2-trichloropropane, 1,1,3-trichloropropane, 1,2,2-trichloropropane, 1,2,3-trichloropropane, tetrachloropropanes, chloro-substituted butanes, pentanes or hexanes or chlorosubstituted aromatic hydrocarbons such as chlorobenzene.

If chlorinated hydrocarbons other than propylene dichloride are used, it will be necessary to make appropriate adjustments to the concentrations of the other components in the system to secure proper operation and it may also be necessary to compensate for the altered physical equilibria by physical modification of the apparatus. For the sake of simplicity, only the use of propylene dichloride will be described.

Either acetic acid or propionic acid can be used as the carboxylic acid. In general we prefer, for ease of operation, to use propionic acid to produce propylene oxide or epichlorhydrin and acetic acid to produce glycidol.

It will be observed that the present process uses hydrogen peroxide and alkene to produce an oxirane with water as the main by-product. Carboxylic acid, sulphuric acid and chlorinated hydrocarbon solvent are essential to the process but are recovered and recycled.

We prefer to use a countercurrent extraction column as the extraction device, but it is also possible to use mixer settlers or some combination.

Dealing with the process of this invention in more detail and as applied specifically to the preparation and use of perpropionic acid, an aqueous phase is supplied to the extraction device, e.g. the upper part of an extraction column, to pass downwardly therethrough. This aqueous phase comprises sulphuric acid, hydrogen peroxide and water. The proportion of sulphuric acid is preferably approximately 45% by weight and is desirably between 30% and 60% by weight. If a lower yield is acceptable then the proportion of sulphuric acid can be between 15% and 85%. Conveniently however for operating reasons the sulphuric acid is derived from 75% by weight sulphuric acid solution in water which forms a feedback from the purification stages which will be described hereinafter, together with make-up acid. The hydrogen peroxide is conveniently approximately 28% by weight of the aqueous phase and in practice between 10% and 35% is very satisfactory. If lower yields are acceptable, then as little as 5% could be used, but above about 35% the mixture could be hazardous. This hydrogen peroxide is of course a fresh reactant and is not a recycle stream and is very conveniently supplied as approximately 70% by weight solution in water. Water makes up the third component of the aqueous phase and its proportions can readily be found by difference.

The organic phase is fed into the lower part of the extraction column to pass upwardly in countercurrent with the aqueous phase and comprises, in the production of propylene oxide, a solution of propionic acid in propylene dichloride. The concentration of propionic acid is preferably between 15% and 30% of the organic phase or conveniently between 10% and 50% by weight.

It should be emphasised that the sulphuric acid performs the dual function of adjusting the specific gravity of the aqueous phase and adjusting the rate of the reaction between hdyrogen peroxide and propionic acid to form perpropionic acid in preference to other competing reactions.

The relative volumes of the aqueous and organic phases and their concentrations together set the ratio between hydrogen peroxide and propionic acid. This ratio is conveniently 1:1 by moles but may be from 1:0.5 to 1:4, or, if low conversions are acceptable, from 1:0.1 to 1:10. However if an excess of hydrogen peroxide is used, it will appear in the effluent from the extraction column and this is undesirable.

The function of the propylene dichloride is to extract the perpropionic acid from the aqueous phase in which it is formed by reaction between the hydrogen peroxide and propionic acid extracted from the organic phase into the aqueous phase. The net result of the operation is to shift the equilibrium in favour of formation of perpropionic acid. Thus in a batch process, even using the preferred composition and employing a 1:1 molar ratio of hydrogen peroxide to propionic acid it is only possible to achieve about 66% conversion of propionic acid or hydrogen peroxide to perpropionic acid. However using the countercurrent system of this invention, over 90% conversion of hydrogen peroxide to perpropionic acid can be obtained.

It may be convenient to carry out a further extraction of the aqueous phase leaving the base of the extraction column using fresh propylene dichloride in order to extract substantially all of both propionic acid and perpropionic acid from the aqueous effluent. It will be understood that in accordance with known extraction techniques, this further extraction can in fact be carried out in the same extraction column. It may also be convenient to use the upper part of the extraction column, or a separate column, to effect a back-wash operation on the organic phase in order to remove dissolved hydrogen peroxide. This can be effected by dividing the aqueous phase into two portions, one being primarily dilute sulphuric acid and the other primarily hydrogen peroxide, and introducing these two portions at spaced locations in the column. It is important to contrast the reaction of the present invention with the more conventional type of reaction in which the hydrogen peroxide would be reacted with the propionic acid in aqueous solution in the presence of sulphuric acid and then the resultant perpropionic acid would be extracted using an organic solvent. This is the type of reaction which has been proposed in the prior art, see for example U.S. Pat. No. 2,813,896.

Two side reactions could in theory occur in the extraction column, namely the reaction of hydrogen peroxide with sulphuric acid to form Caro's acid and the reaction of propionic acid with perpropionic acid to give propionyl peroxide. However the simultaneous extraction into the organic phase constituted by the propylene dichloride has the general effect of minimising these side reactions.

In order to effect the actual epoxidation reaction the solution of perpropionic acid in propylene dichloride from the extraction column is mixed with a molar excess, conveniently of the order of 25% to 50% (although it could be lower or higher) of alkene, e.g. propene, and is then pumped to a suitable reactor, e.g. a pressurised water-cooled tubular reactor. The degree of water cooling is desirably adjusted so as to provide a preferred temperature of about 100° C. If longer residence times or lower yields are acceptable, temperatures in the range 50°–150° C. could be used, but we prefer to operate in the range 75°–120° C. and desirably in the range 90°–100° C. The pressurisation is sufficient to maintain the propene safely in solution at the chosen temperature. If an adequate residence time is allowed in this reactor, for example in excess of 20 minutes and conveniently about 25 minutes in the manufacture of propylene oxide, but depending on temperature, very nearly complete conversion of the perpropionic acid will be achieved and conversions of approximately 99% based on the perpropionic acid can be achieved, with a yield of propylene oxide on perpropionic acid consumed in excess of 98%. It will be understood that with yields of this order, only very small amounts of side reactions take place, the most common being the degradation of perpropionic acid into propionic acid and oxygen or into ethanol and carbon dioxide. There is in addition formation of acetaldehyde, propionaldehyde, propylene glycol or propylene glycol esters and other side products but in general the sum of these do not exceed 2 mol % of the epoxide formed.

The precise physical form of the reactor is not important and we visualise that cocurrent tubular reactors and continuous stirred tanks can both be used, either individually or in some combination. Batch reactors can also be used.

The product mixture from the reactor is taken to a multi-stage distillation process intended to separate out pure product, recycle streams and the impurities. The precise details of the purification process will depend on the alkene and the relationship between its boiling point, that of the oxirane and the other constituents.

In the case of the production of propylene oxide from propylene, the product from the reactor is then conveniently subjected to a stripping operation in order to remove unreacted propylene and this propylene is recovered and recycled to the reactor. The stripped product from the reactor is then suitable for separation by fractional distillation.

Having removed the propylene there are a variety of ways of separating the various components and the preferred method is to effect a multi-stage distillation.

In the first stage, the light fraction comprises the propylene oxide, low boiling point impurities such as acetaldehyde, water and some propylene dichloride. The heavy fraction from this first stage is propionic acid in propylene dichloride and this is recycled but may be distilled to remove heavy impurities such as propylene glycol. The light fraction from the first stage is redistilled in a second stage to give a second light fraction comprising the propylene oxide, acetaldehyde and propionaldehyde and a second heavy fraction comprising water and propylene dichloride which is also recycled. Successive further distillations purify the propylene oxide.

The recycle phases can be passed back to the extraction column as the organic phase after the addition of perhaps minor amounts of propylene dichloride and propionic acid in order to make up for the small inevitable wastage and the purges.

Referring now to the extraction column, it will be recalled that the aqueous phase is supplied to the upper part of the column and is withdrawn from the lower part of the column. As withdrawn from this lower part of the column, the aqueous phase comprises sulphuric acid and water together with perhaps small amounts of hydrogen peroxide although as explained the conditions in the extraction column are preferably such as to ensure almost complete reaction of the hydrogen peroxide. It will be recalled that the second extraction will have removed substantially all the propionic and perpropionic acid from the aqueous effluent. The dilute sulphuric acid is preferably concentrated, desirably by evaporation or distillation, in order to remove the unwanted water and then is recycled to the extraction column.

The modifications necessary to convert the above generalised description relating to propylene to a description relating to propene or any alkene will be apparent to one skilled in the art. Moreover in order that the invention may more readily be understood two embodiments of the same will now be described by way of example and with reference to the accompanying drawings wherein:

FIG. 2 is a flow sheet for the production of epichlorhydrin.

Figure 1:
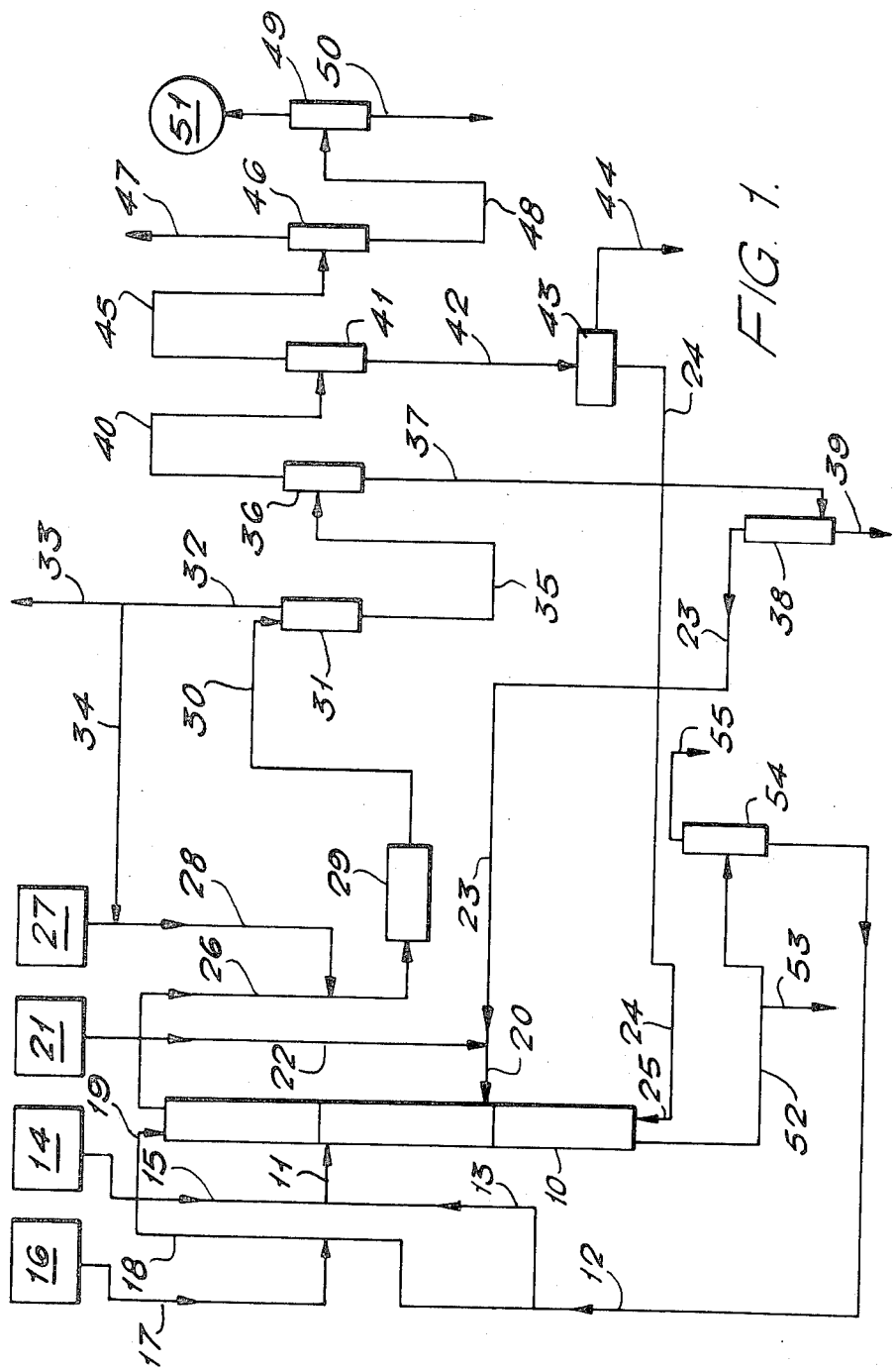
FIG. 1 is a flow sheet for the production of propylene oxide.

The present invention, being a continuous process, is best described with reference to the concentration of reactants flowing in various parts of the system. The figures given correspond to a pilot scale operation but it will be readily understood by those skilled in the art how to scale up to any desired degree.

Referring now to FIG. 1 of the drawings it will be seen that the plant comprises a three-section extraction column 10 to which is fed via an inlet 11 at the top of the centre section an aqueous phase comprising dilute sulphuric acid from recycle lines 12 and 13 and hydrogen peroxide from peroxide storage tank 14 via peroxide supply line 15. The upper section of the column 10 functions as an acid backwash and for this purpose dilute sulphuric acid from the recycle line 12 is mixed with make-up acid from storage tank 16 supplied via line 17 and is fed by a line 18 to an inlet 19 at the top of the column 10. At the bottom of the centre section of the extraction column 10 is an inlet 20 for an organic phase comprising a solution of propionic acid in propylene dichloride and this is supplied from organic storage tank 21 via line 22 and first organic recycle line 23. The lower section of the extraction column 10 constitutes a stripper section and for this purpose is supplied with recycled propylene dichloride which is fed from a second organic recycle line 24 to an inlet 25 at the bottom of column 10.

An organic solution of perpropionic acid in propylene dichloride is withdrawn from the column 10 through line 26, is mixed with propylene supplied from propylene storage tank 27 via line 28 and is fed to a reactor 29.

From the reactor 29, the reaction mixture is taken by line 30 to a stripping unit 31 in order to remove all traces of unreacted propylene. The propylene is withdrawn from unit 31 through line 32 and a portion is passed to purge through line 33 and portion is pumped back through line 34 to join line 28.

The liquid from the stripping unit 31 is passed by a line 35 to a series of four distillation columns. From the first distillation column 36 the heavy fraction is withdrawn through line 37 and passed to a solvent purification column 38. In this column 38 the solvent mixture from line 37 is distilled in order to produce a light fraction which comprises a solution of propionic acid in propylene dichloride which is withdrawn from the column 38 through the line 23 previously referred to as the organic recycle line. The heavy fraction from the solvent purification column 38 is passed to waste through line 39 as a purge. Some or all of the flow in line 37 can be passed directly to line 23, by-passing the purification column 38.

The light fraction from the distillation column 36 is taken by line 40 and passed to second distillation column 41. The heavy fraction from the distillation column 41 is taken by a line 42 to a decanter 43 which separates out an aqueous phase which is passed to waste through line 44. The organic phase from the decanter 43 is taken by the second organic recycle line 24 to be passed back to the extraction column 10. The light fraction from the second distillation column 41 is taken by line 45 to the third distillation column 46 and this column is operated to withdraw a light fraction through a line 47 and pass it to waste. This fraction is in fact substantially acetaldehyde. The heavy fraction from the distillation column 46 is taken by a line 48 and passed to the final distillation column 49 in which it is finally purified to give a heavy fraction which is withdrawn from the column through line 50 and passed to waste, this heavy fraction being substantially completely propionaldehyde. The product is taken from the column 49 and passed to a propylene oxide storage vessel 51.

Reverting now to the extraction column 10, the aqueous phase therein passes out of the base of the column through a line 52 and a proportion is passed to purge through a line 53, this proportion constituting the acid purge. The remainder in line 52 is passed to a distillation column 54 which serves to recover sulphuric acid. In the distillation column 54 the light fraction constitutes chiefly water and is passed to waste through line 55 whilst the heavy fraction constitutes recycle sulphuric acid and is withdrawn from the column 54 by the line 12 and is passed back to the extraction column 10 as previously described.

In order to more fully understand the operation of the plant above described, reference should now be made to Tables I and II which show the mass flow (in kilogrammes/hour) in various parts of the plant described. It will be seen that approximately 70% hydrogen peroxide is used. If 86% hydrogen peroxide were used the only difference would be a reduction of 5 kg/hr water in the raw material stream flowing in line 14 and a corresponding reduction in the water purge from line 55.

TABLE I

| | Raw Material Streams | | | | Recycle Streams | | | |
|---|---|---|---|---|---|---|---|---|
| | 14 | 16 | 21 | 27 | 12 | 23 | 24 | 34 |
| Sulphuric acid | | 1.55 | | | 29.45 | | | |
| Water | 8.41 | 0.03 | | | 15.73 | | 0.32 | |
| Hydrogen peroxide | 19.33 | | | | 0.46 | | | |
| Propionic acid | | | 1.74 | | 0.10 | 60.21 | | |
| Propylene dichloride | | | 0.87 | | | 186.73 | 53.56 | |
| Propylene | | | | 23.70 | | | | 6.73 |
| Others | | | | 0.09 | | | | |
| Perpropionic acid | | | | | 0.01 | | | |

TABLE II

| | Purge Streams | | | | | | | Product Stream |
|---|---|---|---|---|---|---|---|---|
| | 33 | 39 | 44 | 47 | 50 | 53 | 55 | 51 |
| Sulphuric Acid | | 0.04 | | | | 1.55 | | |
| Water | | | 1.30 | | | 1.39 | 15.73 | 0.0005 |
| Hydrogen peroxide | | | 0.37 | | | 0.02 | | |
| Propionic Acid | | | 1.24 | | | 0.01 | | |
| Propylene dichloride | | | 0.74 | | | | 0.02 | 0.0004 |
| Propylene | 0.60 | | | | | | | |
| Others | 0.29 | | | | | | | |
| Perpropionic Acid | | | | | | 0.01 | | |
| Glycols | | | 0.35 | | | | | |
| Propylene Oxide | | | | 0.30 | 0.06 | | | 31.21 |
| Acetaldehyde | | | | 0.12 | | | | 0.0006 |
| Propionaldehyde | | | | | 0.02 | | | 0.0003 |

The plant to produce epichlorhydrin from allyl chloride is illustrated in FIG. 2 and it will be seen that it differs from that to produce propylene oxide chiefly in the purification stages. Thus referring to FIG. 2 the organic solution of perpropionic acid in line 26 is mixed with allyl chloride supplied from allyl chloride storage tank 60 via line 61 and is fed to the reactor 29.

From the reactor 29 the reaction mixture is taken by line 62 to a fractionating column 63 which separates as a light fraction allyl chloride, propylene dichloride and water. This light fraction passes through line 64 to a second fractionating column 65 where allyl chloride is separated as a light fraction and is withdrawn through line 66. A portion of the allyl chloride in line 66 is passed to purge through line 67 and a portion is passed back through line 68 to joint line 61.

The heavy fraction from the second column 65 is taken by line 69 to a decanter 70 which separates out an aqueous phase which is passed to waste through line 71. The organic phase from the decanter 70 is taken by line 72 and is split between the second organic recycle line 24 leading to the bottom of the extraction column 10 and a line 73 leading to a mixing device 74.

The heavy fraction from the first column 63 passes via line 75 to a distillation column 76. The light fraction from the column 76 forms the product and is passed to a product storage tank 77, whilst the heavy fraction passes via line 78 to column 79. In the column 79 the heavy fraction from the column 76 (mainly propionic acid) is distilled in order to produce a light fraction free of heavy impurities. The heavy fraction from the column 79 is passed to waste through line 80 as a purge.

The light fraction from the column 79 is taken via a line 81 to the mixer device 74, where it is mixed with the solution from line 73 and passed into line 23, previously referred to as the organic recycle line.

The remainder of the plant in FIG. 2 is essentially as described with reference to FIG. 1 and in order to more fully understand its operation, reference should now be made to Tables III and IV which show the mass flow (in kilogrammes/hour) in various parts of FIG. 2 described, in so far as they differ from those in FIG. 1.

TABLE III

| | Raw Material Streams | | | | Recycle Streams | | | |
|---|---|---|---|---|---|---|---|---|
| | 14 | 16 | 21 | 60 | 12 | 23 | 24 | 68 |
| Sulphuric acid | | 1.55 | | | 29.45 | | | |
| Water | 8.41 | 0.03 | | | 15.73 | | 0.52 | |
| Hydrogen peroxide | 19.33 | | | | 0.46 | | | |
| Propionic acid | | | 1.74 | | 0.10 | 61.80 | | |
| Propylene dichloride | | | 0.87 | | | | 167.6 | 72.7 |

TABLE III-continued

| | Raw Material Streams | | | | Recycle Streams | | | |
|---|---|---|---|---|---|---|---|---|
| | 14 | 16 | 21 | 60 | 12 | 23 | 24 | 68 |
| Allyl chloride | | | | 43.67 | | | | 36.73 |
| Perpropionic acid | | | | | 0.01 | | | |

TABLE IV

| | Purge Streams | | | | | Product Streams |
|---|---|---|---|---|---|---|
| | 67 | 71 | 80 | 53 | 55 | 77 |
| Sulphuric acid | | | 0.04 | 1.55 | | |
| Water | | 1.30 | | 1.39 | 15.73 | |
| Hydrogen peroxide | | 0.37 | | 0.02 | | |
| Propionic acid | | | | 1.24 | 0.01 | |
| Propylene dichloride | | | | 0.01 | 0.02 | 0.001 |
| Allyl chloride | 1.06 | | | | | |
| Others | 0.39 | | | | | |
| Perpropionic acid | | | | 0.01 | | |
| Glycols | | 0.95 | | | | |
| Epichlorhydrin | | | | | | 49.27 |

It will be seen from these embodiments of the invention that the main inputs are hydrogen peroxide and propene (propylene or allyl chloride) with very minor make-up amounts of sulphuric acid, propionic acid and propylene dichloride. The recycle streams and purge streams emphasise that under the conditions, the process of this invention produces the epoxide (propylene oxide or epichlorhydrin) at high yield and purity.

We claim:

1. A continuous process for the production of a peracid in a chlorinated hydrocarbon solvent comprising the steps of:
    (a) providing an aqueous phase comprising sulphuric acid, hydrogen peroxide and water;
    (b) providing an organic phase comprising a chlorinated hydrocarbon solvent and carboxylic acid selected from the group consisting of acetic acid and propionic acid; and
    (c) contacting said aqueous and organic phases countercurrently to produce an aqueous solution comprising sulphuric acid and water and an organic product solution comprising chlorinated hydrocarbon solvent and a peracid corresponding to said carboxylic acid.

2. The process of claim 1, including the added step of:
    (d) utilising at least a portion of said aqueous solution to provide at least a portion of the aqueous phase of step (a).

3. The process of claim 2, wherein the aqueous solution is concentrated by the removal of water prior to being used as a portion of the aqueous phase.

4. The process of claim 1, wherein the proportion of sulphuric acid in the aqueous phase is between 30% and 60% by weight.

5. The process of claim 1, wherein the proportion of hydrogen peroxide in the aqueous phase is between 10% and 35% by weight.

6. The process of claim 1, wherein the proportion of carboxylic acid in the organic phase is between 15% and 30% by weight.

7. The process according to claim 1, wherein the relative volumes and concentrations of the organic and aqueous phases are such that the molar ratio of hydrogen peroxide to carboxylic acid is between 1:0.5 to 1:4.

8. A process for the production of an oxirane comprising:
    (a) providing an aqueous phase comprising sulphuric acid, hydrogen peroxide and water;
    (b) providing an organic phase comprising a chlorinated hydrocarbon solvent and carboxylic acid selected from the group consisting of acetic acid and propionic acid;
    (c) continuously contacting said aqueous and organic phases countercurrently to produce an aqueous solution comprising sulphuric acid and water and an organic product solution comprising chlorinated hydrocarbon solvent and a peracid corresponding to said carboxylic acid; and
    (d) reacting at least a portion of the peracid in said organic solution with an alkene to produce an oxirane.

* * * * *